United States Patent [19]

McAdams

[11] Patent Number: 5,120,122
[45] Date of Patent: Jun. 9, 1992

[54] SIMULTANEOUS STEREO FUNDUS CAMERA

[75] Inventor: John B. McAdams, Santa Monica, Calif.

[73] Assignee: Nishika Limited, Henderson, Nebr.

[21] Appl. No.: 490,305

[22] Filed: Mar. 8, 1990

[51] Int. Cl.⁵ .............................................. A61B 3/14
[52] U.S. Cl. .................................... 351/206; 351/211
[58] Field of Search ............... 351/206, 211, 214, 221; 354/62

[56] References Cited

U.S. PATENT DOCUMENTS 4,715,703  12/1987  Cornsweet et al. ................. 351/206

FOREIGN PATENT DOCUMENTS 4003211  8/1990  Fed. Rep. of Germany .
61-45721  3/1986  Japan .

Primary Examiner—Paul M. Dzierzynski
Attorney, Agent, or Firm—Brumbaugh, Graves, Donohue & Raymond

[57] ABSTRACT

This invention relates to an improved simultaneous stereo retinal camera capable of generating repetitive images from different cameras and at different times for diagnostic purposes. A Helium Neon laser light source located integrally with the optics of the camera generates a fixation indicia for the left and right eye of the patient and a scaler indicia located in the field of view of the camera and printed on each stereo photograph. The patient fixates on either the left or right indicia which places the optic nerve in the field of view of the camera. The scaler indicia appearing on the photo provides the basis for generating a standardized 3-D photo regardless of the camera used.

10 Claims, 3 Drawing Sheets

SIMULTANEOUS STEREO FUNDUS CAMERA

The present invention is concerned generally with cameras of the type known as a simultaneous stereo fundus cameras capable of generating three dimensional images (3-D) for the scientific community.

In ophthalmology, photography and stereo (3-D) photography have been used for documentation and evaluation of medical conditions. In the past, so called 3-D images were not true simultaneous photographs since each photo was made at a slightly different perspective and at different times by first shooting one frame and then moving the camera to one side to t a second frame. The resulting images reduced to slide format were then viewed on a light box with 8 or 10 diopter loupes, similar to those used in aerial stereo photography to obtain the 3-D effect.

The primary application for such technology has been in the medical field and specifically in the ophthalmology field the examination and evaluation of the optic nerve head and fundus. Presently many cameras are known generally as Simultaneous Stereo Retinal Cameras of the type made and sold by Topcon Instrument Corporation of America located in New Jersey under the name TRC-SS2 and TRC-SS.

The present invention will describe an improvement in Simultaneous Stereo Retinal Cameras as it applies to ophthalmology and the examination of the optic nerve head. It is believed or known that early detection of changes in the shape (cupping) of the optic nerve head can be used to detect and treat glaucoma.

The improvement described for the Fundus Camera can be used with any Simultaneous Stereo Fundus Camera and as a result there are many medical and scientific applications of which the fundus application is only one.

Glaucoma, for example, is a condition of the eye in which there is a change in the optic nerve head contour usually accompanied by increased intra-ocular pressure and subsequent loss of field of vision often resulting in irreversible blindness. However, if glaucoma is detected and intraocular pressure reduced to normal or tolerable levels by medication or surgery, the progression of blindness can be arrested completely or reduced. Lack of standardized Stereo Photography of the optic nerve head prevented the camera technique from being the definitive diagnostic tool of glaucoma prior to the present invention.

Because glaucoma is so often asymptomatic, early diagnosis depends currently in large measure on the routine measurement of intraocular pressure with a tonometer, the routine funduscopic examination of the optic nerve head (optic disc) with an ophthalmoscope and sequential stereo photography of nerve head, and the routine examination of visual fields. It was believed that by using all three office procedures, that early detection of glaucoma was possible. By utilizing this standardized camera and processing, a definitive diagnosis may be made without needing pressure and field of view measurements.

For any given person the factors affecting the rate of aqueous production, the rate of aqueous outflow and the volumes of other tissues within the eye are in a state of dynamic equilibrium. Unfortunately, if fluid production exceeds outflow because of increased production or decreased outflow or both, intraocular pressure will increase. Once intraocular pressure increases above the tolerance of the optic nerve, the optic nerve atrophies and blindness may result.

Visual damage resulting from glaucoma follows a progressive and distinctive pattern of development. Chronic elevation of intraocular pressure has relatively little effect on blood flow through the central retinal artery. However, it is believed that increased intraocular pressure can have dire consequences on the small and partially extraocular vessels that supply the optic nerve fibers in the region of the lamina cribrosa.

At first, axonal damage, secondary to glaucoma is reversible. Later, it is permanent, and atrophy of the axon occurs. The optic nerve, more properly considered a brain tract, does not regenerate atrophic axons.

Complicating the diagnosis of glaucoma is the fact that measurement of intraocular pressure alone is insufficient to establish or eliminate glaucoma as a diagnosis. There are persons having a high intraocular pressure that show no evidence of optic nerve change or visual field loss despite pressure remaining at a high level of over 35 mm. Hg for several years. For such persons the term ocular hypertension without glaucoma is used. In other words, simply measuring the internal ocular pressure is not necessarily an indication of glaucoma.

Early detection of glaucoma depends on recognizing contour change in the optic nerve disc which indicates pressure induced optic nerve injury.

The normal optic nerve head has a depression, which is usually centrally placed, called the physiologic cup. This cup is variable in size, shape, and contour from one individual to another. Within the disc, the physiologic cup appears as a depression, generally placed centrally, with the ratio of cup diameter to disc diameter usually being 0.3 (30%) or less.

The depth of the cup varies from person to person. The degree of cupping is less marked in far-sighted individuals than in persons without significant refractive error. In some individuals, the depth of the cup may be so great that the gray reticular outline of the lamina cribrosa is visible at the base of the cup.

The first evidence of glaucomatous change is often a notching of the cup contour. This notching is located on the rim of the cup and is often associated with a slight pallor of the rim. As loss of axons continues because of uncontrolled glaucoma, the cup begins to deepen, often becoming deepest just proximal to the notching, that is, toward the central area of the optic nerve. Soon, the lamina cribrosa becomes visible within the cup.

It can be appreciated therefore, that glaucoma causes irregularity of cup contour, increase in the depth of the physiologic cup, exposure of the lamina cribrosa, nasal displacement of the central retinal vessels, and pallor of the optic nerve head progressively affecting the entire optic disc.

Most important, is the fact that changes in the optic precede recognizable visual field loss and tonometric pressure changes.

The classical changes found in the nerve head in well established glaucoma are not difficult to recognize; however, the earliest changes in the cup constitute a true diagnostic challenge that was not available until the present improvement to the Simultaneous Stereo Fundus Camera.

Present day Stereo Fundus Cameras take excellent 3-D photos which allow the physician to examine the cup of the optic nerve and the lamina cribrosa if visible. Unfortunately, serial photos are necessary to view a trend in the changes in the optic nerve over a period of time.

In order to use the photos from a fundus camera as a diagnostic tool it is necessary that each camera take a photo from the same unique position as every other photo in order to assure that no positional change has taken place. The problem is compounded when photos are taken with different cameras and the results reviewed for examination and diagnosis. Without assurances that each photo was taken from the same unique position, the photos can not be used for quantitative analysis. A qualitative review can be made, but here again the results are suspect without assurance that each photo was taken from the same unique position. Observed changes could be the result of eye movement, positional camera changes, photo processing reference changes or by true changes in the eye of the patient itself.

In the present invention a laser light source is incorporated in the optics of a simultaneous stereo fundus camera and is used to generate a left and right fixation beam and a scaler indicia that is printed on the resulting photographs and used to produce standardized 3-D photographs.

The laser beam is par focal, meaning it has the same focal length as the camera, and eminates from the camera at the exact same angle and position each time the patient is asked to look at the red fixation light. In this way the optic nerve head is uniquely presented in the field of view of the camera each and every time for each photo taken.

The scaler indicia generated from the same laser and projected into the eye of the patient is recorded on each stereo photograph and is used by the processing equipment in the 3-D photograph. Because the optics are fixed and par focal, the scaler indicia appears in the same unique position in every photograph. Any change in the size of the scaler indicia appearing in the photograph will be a function of the eye itself and hence the scaler indicia can be used as a measuring tool to make direct quantitative measurements of elements in the eye. With the present invention standardization now allows examination of quantitative and qualitative changes in the eye directly from the 3-D photographs regardless of when the photos were made or which camera made the pictures.

Standardization of eye position is assured by having a projection laser beam that is par focally optically fixed to the camera optics both angularly and positionally. Once standardization is achieved the following benefits become possible:

1. Standardized fixation allows the eye to be viewed and photographed from exactly the same position in serial patient sittings;
2. The scaler indicia provides a standardized depth of focus (registration) generating a reference point in the eye for processing the film. Standardized depth of focus scaler indicia provides a reference point in the eye for comparison of serial changes both quantitative and qualitative, in measuring the changes of various structures in the eye.
3. The standardized gray color scale is used as a color reference in film processing, also the standardized gray bar is used as a reference means to account for changes in the color of the eye regardless of changes in flash setting, illumination changes, or changes in the film emulsion which occur as a function of time;
4. Standardized film processing assures electro-optical and chemical balancing of the end product by using the same films;
5. Standardized simultaneous stereo photography of the optic nerve head is based on the unique scaler indicia markings on the photograph;
6. Standardized lenticular-viewed optic disc stereo photographs is based on the the unique scaler indicia markings on the photograph;
7. Standardized scaler indicia imprinted on the photograph is used to make quantitative measurements from each photograph; and
8. Standardized color references imprinted on the photograph provides a color comparison for different objects viewed on the photograph.

Further objects and advantages of the present invention will become more apparent by referring now to the accompanying drawings wherein.

In the preferred embodiment a Simultaneous Stereo Retinal Camera is used to take pictures of the inside of the eye with the pupil dilated. The camera consists of a camera back on an optical system that provides coaxial ambient illumination for viewing, coaxial flash for photography and optics that compensate for the eye's own powerful optical system to permit focusing on specific intraocular structures. Basic fundus cameras are illustrated in U.S. Pat. Nos. 4,756,613, 4,187,014 and 4,208,107.

Figure 1:
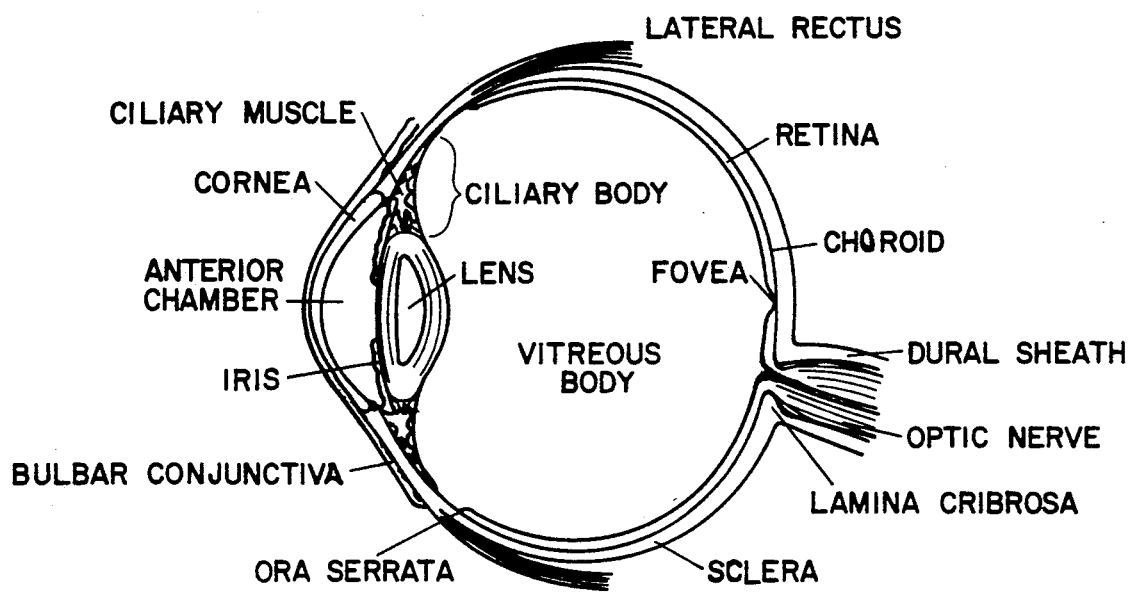
FIG. 1 is a cross section of an eye showing the basic anatomy of the eye and related structures pertinent to glaucoma detection.
Figure 2:
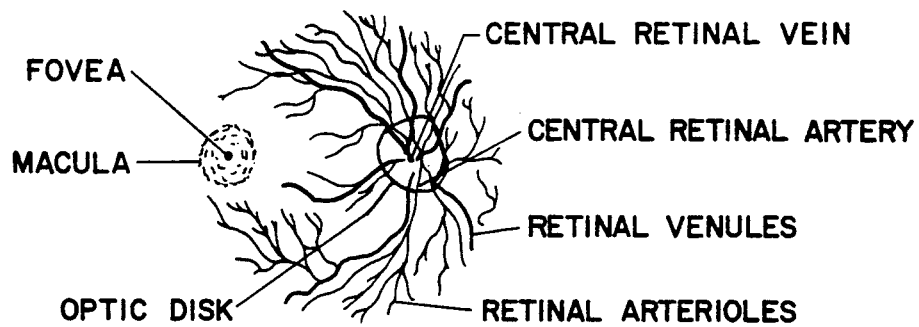
FIG. 2 is an exploded view of the optic nerve illustrated in FIG. 1 more fully showing the relationship between the fovea and the macula.

The basic anatomy of the eye is more fully illustrated in FIG. 1 and 2 which illustrates the internal related structures pertinent to the glaucoma detecting system to be described. By way of definition, the fovea is a depression in the macula. Because of the depression the fovea is essentially at the same depth plane from the cornea. Therefore, with the patient looking directly at an object, the object being viewed (usually a red light) is focused on the macula leaving the optic nerve, which is displaced, in the field of view of the camera.

The prior art recognized that having the patient focus on a remote light source (usually red), would result in the light being focused on the fovea and the optic nerve would be in the field of view of the fundus camera. In some cameras the light source was external not par focal and moveable and in other cameras the light source was internal but also moveable. Allowing the light source to be moveable provided a convenient means for moving the object being viewed in the field of view of the camera but at the same time prevented the standardization achieved by the present invention.

In the preferred embodiment a red line laser, such as a helium-neon laser is optically incorporated in a fundus camera in a par focal fixed coaxial position with respect to the optical light source of the camera. A beam splitter generates the left and right fixation points which are outside the field of view of the camera and the scaler indicia which is inside the field of view of the camera. It is the fixed position of the red line laser and the resulting par focal scaler indicia that provides the standardized 3-D photograph which allow quantitative measurements to be made from photographs made with different cameras.

The par focal projected laser beam is caused to eminate at the exact same angle and position each time the patient looks at the red light. In this way the optic nerve is presented in exactly the same perspective in the camera field of view each and every time. The projected laser beam split into a left and right fixation beam that is viewable by the patient but is otherwise outside the field of view of the camera. The projected laser beam also produces a scaler indicia that is photographically recorded and used by the film processors to generate the standardized 3-D photographs. Standardization of eye position is assured because the projected laser beam is fixed, camera to camera par focally, angularly and positionally. The optical lens system of the stereo camera provides the means for the camera to take a pair of pictures as selected by the operator.

Figure 3:
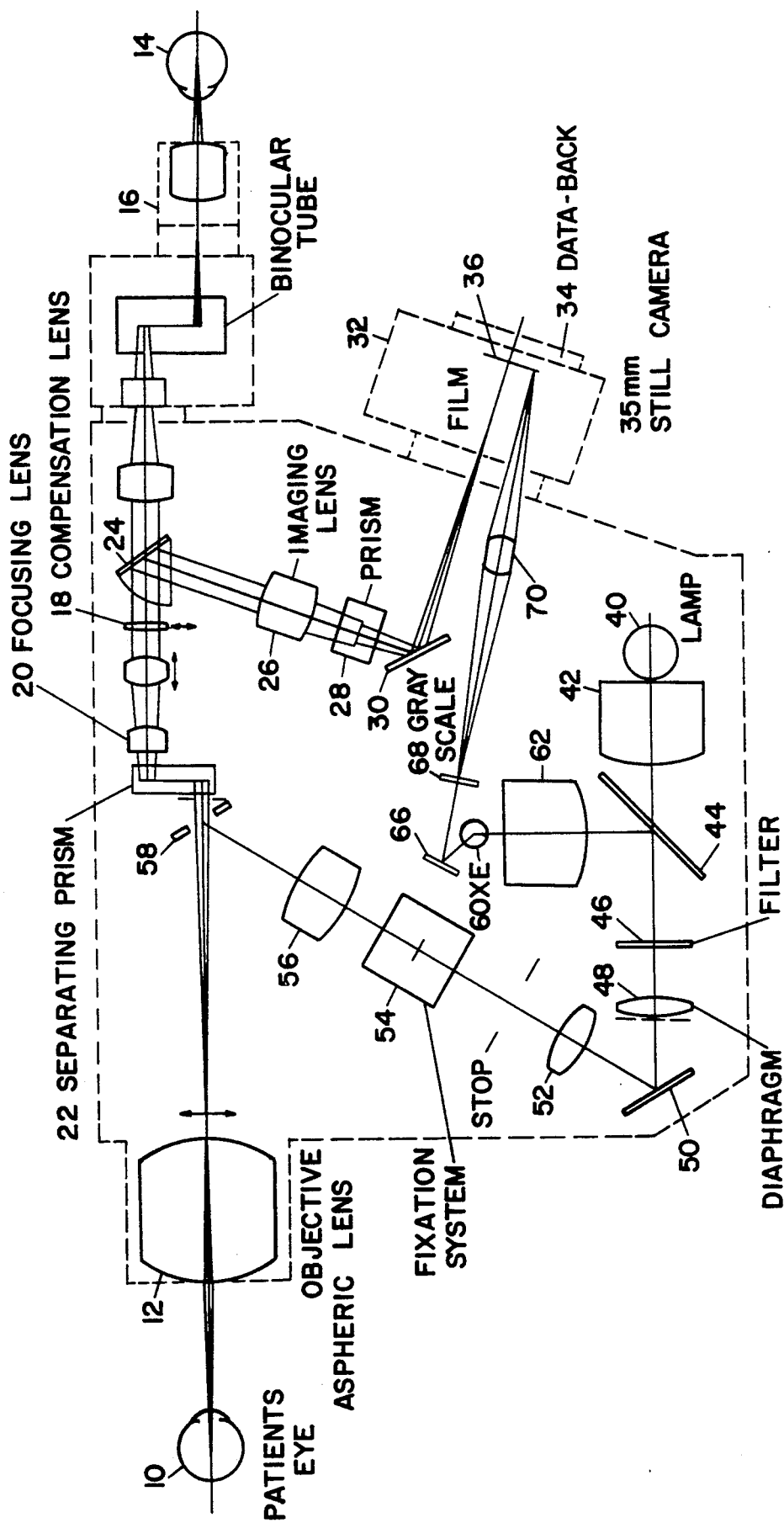
FIG. 3 illustrates an optical diagram for a simultaneous stereo fundus camera having an internal fixation system.

As shown in FIG. 3 either the left or right eye of the patient 10 is located in front of an aspheric lens 12 having a shape approximating the curvature of the fundus to thereby compensate for the curve of the eye. The operator 14 has a binocular eyepeice 16 for viewing the eye 10 through a compensating lens 18, a focusing lens 20 and a separating prism 22 which directs the viewing beam to the aspheric lens 12. The actual viewing system for the operator 14 is a conventional stereo binocular observation system 16.

In order to take photographs of the view selected by the operator 14, the viewing beam is interrupted by a pivoting mirror 24 that is aligned with an imaging lens 26 that focuses the reflecting light beam to a prism 28. The light beam is directed to a mirror 30 which reflects the light beam to a still camera 32 having a data back 34 and film 36 for recording the selected scene. In the normal position, the swing mirror 24 is horizontal which allows the light beam to pass directly to the operator. It is only when the operator desires to take a photograph that the mirror is erected as shown, to momentarily direct the light beam to the camera 32.

The light necessary to allow the operator 14 to view the eye 10 is supplied by a conventional light source 40. Light source 40 is directed through a condensing lens 42, through a fixed beam splitter 44, to a fixed conventional mirror 50.

Mirror 50 directs the light from source 40 through condensing lens 52 and preferably through a coaxial fixation system 54 capable of generating the left and right fixation indicia and the scaler indicia more fully described in connection with FIG. 5. All light passing from the fixation system 54 passes through a condensing lens 56 and is directed to a beam splitter 58 associated with the viewing system for directing all light both to the eye 10 and either to the operator 14 or the film 36 depending on the position of the swinging mirror 24.

In order to take a photograph, a xenon flash tube light source 60 under the control of the operator is used. When the operator 14 determines that the object being viewed is worthy of a picture, a sequence of events is initiated that causes light source 60 to flash and mirror 24 to erect so as to reflect the light back to the film 36 in the camera 32.

The light eminating from the light source 60 is directed primarily to a condensing lens 62 which directs the light to the fixed mirror 44 and eventually through the same light path described for lamp 40 to split mirror 58 which directs the light flash to the patients eye 10. The reflected light from the eye 10 passes through the beam splitter 58 back to the rotating mirror 24 which is now erected for reflecting the light to fixed mirror 30 which directs the light to the camera 32 and film 34. The actual technique for viewing the scene and taking the picture are well know in the state of the art and are fully described in the cited patents.

An important addition to taking the picture is the implanting on the film itself a gray scale that can be used by the viewer of the resulting photograph as a color guide to the actual color of items in the photo and to color balance the processing.

A portion of the light from the source 60 is reflected by a mirror 66 through a gray scale 68 to an imaging lens 70 that directs the gray scale image to a special portion on the film 34. Changes in the light source or changes in the emulsion on the film which could affect the color of items on the photo is eliminated. The gray scale 68 is used to determine the relative hue and color of items in the photo regardless of light changes or emulsion changes. In addition, changes in the optical characteristics of the light source used in producing the 3-D image will not effect the relative characteristics of the colors in the photo. In this way a standard located on the film itself is established that is viable over time regardless of change.

Figure 4:
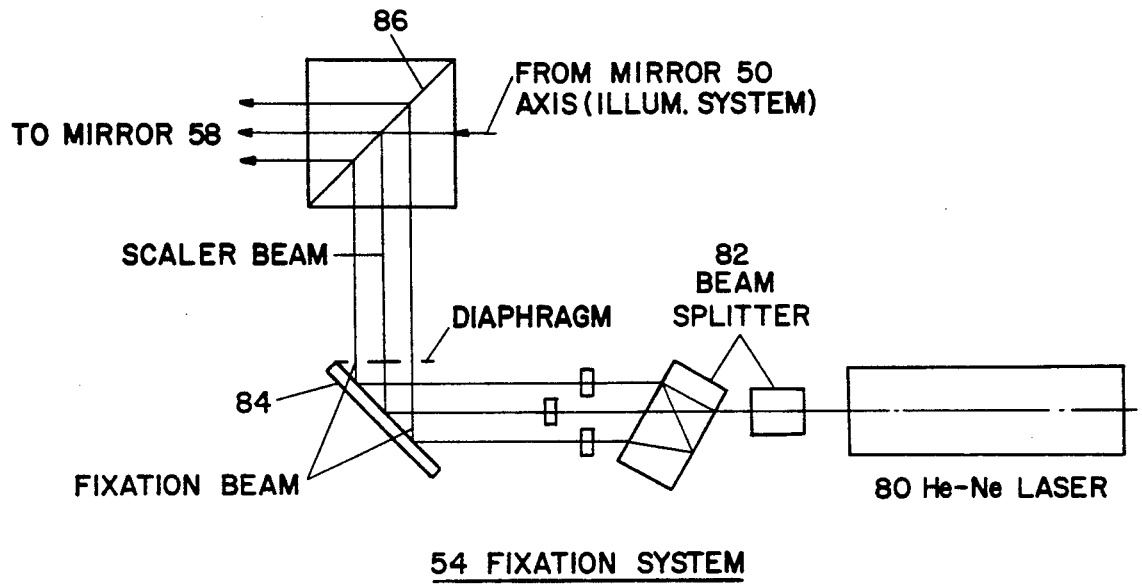
FIG. 4 illustrates a fixation system for generating an internal fixation and scaler indicia for the system illustrated in FIG. 3.

Referring now to FIG. 4 there is shown in more detail the components of the fixation system 54 described in connection with FIG. 3. The fixation system 54 is preferable mounted coaxial with the light path from mirror 50 to mirror 58 as illustrated in FIG. 3.

A separate light source from a laser 80 (typically helium-neon) generates a red light beam that is fed to a beam splitter 82 which produces three (3) separate par focal indicia images; a dot for the right eye fixation, a dot for the left eye fixation and a scaler indicia preferably in the form of a cross having a given dimension in each direction. All three indicia are fed to a mirror 84 which directs the three beams to a mirror 86 that is located on the axis of illumination from mirrors 50 to 58 as illustrated in FIG. 3.

As will be described in connection with FIG. 5, the scaler indicia is positioned to be located in the field of view of the objective lens of the camera while the left and right fixation points are not located in the field of view of the camera.

Figure 5:
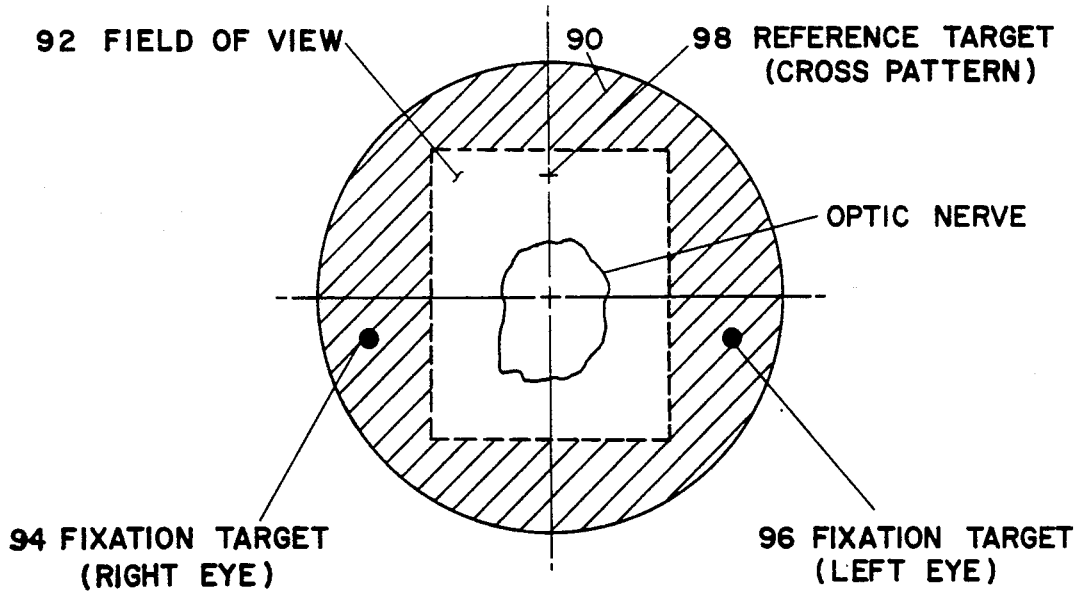
FIG. 5 illustrates the fixation target for the right and left eye and the scaler indicia as viewed by the field of view of the camera.

Referring now to FIG. 5 there is shown the projected illumination 90 shown as shaded, with the field of view of the camera shown as 92. The right fixation point 94 and the left fixation point 96 are both outside the field of view of the camera 92 and at a position below the center line of the field of view of the camera 92. A review of FIG. 1 will show that the fovea is located above the optic nerve and it is for this reason that both the right and left fixation points 92 and 94 are located below the center line of the field of view 92 in order to place the optic nerve in the center of the camera field of view.

The par focal scaler indicia 98 is carefully configured when projected to have a given length and width say of the order of 1.5 mm vertical and 0.75 mm horizontal. The resulting indicia 98 as it appears in the field of view 92 is changed by the size, shape and condition of the patients eye and hence the actual size of the indicia appearing in the photograph will be different in size from that projected. The change in the size of the scaler indicia that appears on the photograph is a function of the eye thereby allowing the observer to make quantitative measurements of items in the photo based on the size of the scaler indicia 98.

In the actual stereo camera the patient only sees the right and left indicia 94 and 96 and does not see the scaler indicia 98. The actual projection of the scaler indicia 98 is flashed on the field of view 92 only when the operator takes a picture and energizes the light source 60 as explained in connection with FIG. 3. In order to place the optic nerve in the center of the field of view 92 the patient must focus on either the right or left fixation points 94 or 96. The scaler indicia 98 is needed only by film processing equipment in the 3-D photo and its interpretation and in fact might be confusing to the patient if it were in his field of view.

The par focal scaler indicia 98 is fixed optically to the fundus camera and hence becomes the point of standardization used by the film processors in producing the 3-D photos taken by the stereo camera. In this way all 3-D photos can be compared both quantitatively and qualitatively regardless of which cameras took the pictures.

The stereo fundus camera has been described primarily in connection with an application to examining the retina of the eye. The concept of projecting a scaler indicia in the field of view of any stereo camera will lead to the same benefits and advantages described for the simultaneous stereo retinal camera.

I claim:

1. A stereo camera capable of simultaneously taking a pair of pictures for processing into a 3-D photograph, comprising:
   stereo optics for observing and photographing selected objects in a preferred field of view; and
   a light beam integrally associated with said stereo optics for projecting a scaler indicia in the form of a cross that is located in said field of field so as to be recorded on the resulting photographs, the projected dimensions of said cross being substantially 1.5 mm by 0.75 mm.

2. A stereo Camera capable of simultaneously taking a pair of pictures for processing into a 3-D photograph comprising;
   stereo optics for observing and photographing selected objects in a preferred field of view;
   a light beam integrally associated with said stereo optics for generating a scaler indicia that is projected on the object being viewed and is located in said field or view whereby said scaler indicia location is recorded on the resulting photographs; and
   a gray scale projected directly on a portion of each resulting photograph by the same light source used to illuminate the patients eye.

3. A stereo Fundus Retinal Camera capable of simultaneously taking a pair of pictures for processing into a 3-D photograph comprising;
   stereo optics for observing and photographing the optic disc of the eye of a patient;
   a light beam integrally associated with said stereo optic for generating and projecting a light beam into the eye of the patient;
   beam splitter means for splitting said light beam into a left and right fixation beam and a scaler indicia;
   projection means for projecting said left and right fixation beam out of the field of view of the camera while said scaler indicia is projected in said field of view whereby said scaler indicia is recorded on the resulting photographs.

4. A Stereo Fundus Retinal Camera according to claim 3, in which said light beam is located coaxial with said stereo optics of said camera.

5. A Stereo Fundus Retinal Camera according to claim 3 in which said light is par focal with said camera.

6. A Stereo Fundus Retinal Camera according to claim 3 in which said light beam is fixed in relationship with said stereo optics of said camera.

7. A Stereo Fundus Retinal Camera according to claim 3 which includes means for projecting said scaler indicia on said field of view only at the time of actually taking said photographs.

8. A Stereo Fundus Retinal Camera according to claim 3 which includes a grey scale projected directly on a portion of each resulting photograph by the same light source used to illuminate the patients eye.

9. A Stereo Fundus Retinal Camera according to claim 3 in which said light beam is a laser beam.

10. A Stereo Fundus Retinal Camera according to claim 9 in which said laser beam is generated by a Helium-Neon light source.

* * * * *

UNITED STATES PATENT AND TRADEMARK OFFICE
CERTIFICATE OF CORRECTION

PATENT NO. : 5,120,122
DATED : June 9, 1992
INVENTOR(S) : John B. McAdams

It is certified that error appears in the above-identified patent and that said Letters Patent is hereby corrected as shown below:

Title Page, Item 73, "Nebr." should read --Nev.--.
Col. 1, line 14, "to t" should read --to take--;
Col. 3, line 35, "in" should read --in generating--;
Col. 7, line 16, "in" should read --in making--;
Col. 7, line 41, "field of field" should read --field of view--;
Col. 8, line 6, "field or view" should read --field of view--.

Signed and Sealed this

Fifth Day of July, 1994

Attest:

BRUCE LEHMAN

Attesting Officer

Commissioner of Patents and Trademarks